United States Patent
Chan et al.

(10) Patent No.: US 6,223,129 B1
(45) Date of Patent: *Apr. 24, 2001

(54) APPARATUS AND METHOD FOR CONDUCTIVITY MEASUREMENT INCLUDING PROBE CONTAMINATION COMPENSATION

(75) Inventors: Wai Yin Cedric Chan; James W. Livingston, both of Santa Cruz, CA (US)

(73) Assignee: Diverseylever, Inc., Plymouth, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/078,400

(22) Filed: May 13, 1998

(51) Int. Cl.$^7$ .................................................. G01N 27/48
(52) U.S. Cl. .............................. 702/30; 324/439; 137/392
(58) Field of Search ................................ 702/30, 32, 50; 324/439, 691; 137/392, 5; 73/335.05; 422/82.02

(56) References Cited

U.S. PATENT DOCUMENTS

| | | |
|---|---|---|
| 4,119,909 | 10/1978 | DeBerry . |
| 4,756,321 | 7/1988 | Livingston et al. . |
| 4,808,930 | 2/1989 | Kaiser . |
| 5,025,220 * | 6/1991 | Colvin et al. ........................ 324/449 |
| 5,260,663 * | 11/1993 | Blades ................................... 324/442 |
| 5,334,940 * | 8/1994 | Blades ................................... 324/442 |
| 5,453,131 | 9/1995 | Chan et al. . |
| 5,500,050 | 3/1996 | Chan et al. . |
| 5,543,717 * | 8/1996 | Kordas ................................... 324/444 |
| 5,581,189 * | 12/1996 | Brenn ................................... 324/439 |
| 5,647,391 | 7/1997 | Chan et al. . |
| 5,973,503 * | 10/1999 | Kuipers et al. ....................... 324/698 |

FOREIGN PATENT DOCUMENTS 288 099   10/1988  (EP) .

* cited by examiner

Primary Examiner—Patrick Assouad
(74) Attorney, Agent, or Firm—Pennie & Edmonds LLP

(57) ABSTRACT

A conductivity measurement system provides one or more DC pulses to first and second electrodes submerged in an aqueous solution such as, for instance, the wash water of an industrial dishwasher. The voltage at the first electrode is measured at first and second predetermined times after initiation of DC pulse(s). Linear regression of the first and second measured voltages is used to calculate the voltage at the first electrode at the beginning of the DC pulse(s), i.e., at time t=0. The resulting voltage at time t=0 is then used to calculate the conductivity of the solution, thereby compensating for the effects of polarization. Further, the difference between the respective first and second measured voltages is compared to a predetermined threshold value to determine whether the electrodes are so contaminated that polarization compensation is no longer feasible, thereby signaling that the electrodes should be cleaned or replaced.

29 Claims, 4 Drawing Sheets

APPARATUS AND METHOD FOR CONDUCTIVITY MEASUREMENT INCLUDING PROBE CONTAMINATION COMPENSATION

BACKGROUND

1. Field of Invention

The present invention relates generally to conductivity measurement systems and the low-cost probes thereof, such as used in commercial dishwashers, and particularly to conductivity measurement systems which compensate for probe contamination.

2. Description of Related Art

Industrial dishwashers use conductivity measurement systems to maintain proper detergent concentrations in the dishwashers' wash water. Conductivity measurement systems are well known and typically include a probe that has first and second electrodes submerged in the wash water. A signal from a source circuit is applied to the electrodes to induce a current between the electrodes. This current, which is mirrored in the source circuit, is determined by dividing the voltage in the source circuit by the impedance of the source circuit. The conductivity of the wash water is then determined by dividing the current between the electrodes by the voltage across the electrodes.

Current flow in an aqueous solution, e.g., the wash water, is facilitated by the flow of ions between the electrodes. In an industrial dishwasher, the ions are provided by the detergent. Thus, increasing the detergent concentration results in a corresponding increase in the conductivity of the wash water. The relationship between wash water conductivity and detergent concentration for a particular detergent is typically stored in a look-up table, thereby allowing detergent concentration to be easily derived from wash water conductivity.

As current is induced between electrodes in an aqueous solution, ions begin accumulating on one of the electrodes. The ions accumulating on the electrode surface each occupy a finite space such that after a time period t there is no more available surface area on the electrodes on which ions may accumulate. This phenomena, known in the art as polarization, reduces current flow between the electrodes and may result in erroneous conductivity measurements which, in turn, lead to erroneous detergent concentration measurements. Thus, when the electrodes become polarized, the detergent concentration of the wash water is perceived by the dishwasher to be too low, thereby leading to the addition of detergent to wash water that may, in reality, already be of a desired detergent concentration.

Further, when used as described above, the electrodes undesirably accumulate non-conductive particles thereon which, in turn, reduce the effective area of the electrodes. As a result, contamination of the electrodes speeds the above-described polarization of the electrodes and, therefore, diminishes the useful life of the electrodes.

In theory, the effect of polarization upon conductivity measurements can be eliminated by calculating conductivity the instant current is induced between the electrodes, since at time t=0 ions have not yet accumulated on the electrodes. Here, the voltage between the electrodes must be measured just as the source signal that induces current in the wash water is asserted. Unfortunately, such an approach is not feasible. First, there are significant characteristic variations between ion species during the first 1–2 microseconds of aqueous current flow. Since the ion species of the detergent is typically unknown, measurements taken within the first 1–2 microseconds are unreliable. Second, it is very difficult to fabricate a circuit which can produce a source pulse and then immediately capture an analog reading produced by the source pulse.

U.S. Pat. No. 4,756,321 discloses an industrial dishwashing system in which a continuous AC signal is applied to first and second electrodes submerged in wash water to induce a current between the electrodes. The resulting current is measured over time, and then used to calculate the conductivity of the wash water. Conductivity is then converted into a logarithmically scaled detergent concentration. Here, the continuous current flow between the electrodes results in a continually increasing polarization of the electrodes. As a result, the electrodes must be either cleaned or replaced at regular intervals. The servicing of the electrodes is not only expensive, but also reduces operating efficiency of the dishwasher. Further, this system's inability to measure or predict electrode contamination makes it even more difficult to optimize the useful life of the electrode.

Another approach involves driving the electrodes with a pulsed DC signal as described, for instance, in U.S. Pat. No. 4,119,909. In that system, the pulsed DC signal induces short pulses of current between the electrodes in the wash water. Use of short current pulses reduces polarization and, thus, increases the useful life of the electrodes, as compared to the averaging technique disclosed in U.S. Pat. No. 4,756,321. However, conductivity measurements provided by this approach are nevertheless influenced by polarization. Further, this system, like that disclosed in U.S. Pat. No. 4,119,909, is unable to measure or predict electrode contamination. It is therefore difficult to accurately determine when or at what rate the measured conductivity deviates from the actual conductivity and, as a result, the accuracy with which this approach maintains the detergent concentration at a target level is compromised. It is thus also difficult to maximize the intervals at which the electrodes are cleaned or replaced and, therefore, difficult to maximize the useful life of the electrodes.

SUMMARY

An apparatus and method for measuring conductivity of an aqueous solution are disclosed which compensate for polarization and provide warning of electrode contamination. In accordance with the present invention, one or more DC pulses are applied to first and second electrodes submerged in an aqueous solution such as, for instance, the wash water of an industrial dishwasher. The voltage at the first electrode is measured at first and second predetermined times after initiation of the one or more DC pulses. The difference between the respective first and second measured voltages is calculated and then compared to a predetermined threshold value. If the difference voltage exceeds the predetermined threshold value, thereby indicating that the electrodes are sufficiently contaminated so as to soon require cleaning or replacement, an alarm signal is asserted. In this manner, present embodiments maximize the useful life of the electrodes and, thus, minimize servicing costs.

Further, present embodiments provide conductivity measurements compensated for polarization. Linear regression of the first and second measured voltages is used to calculate the voltage at the first electrode at the beginning of the one or more DC pulses, i.e., at time t=0. The resistivity of the solution is calculated using Ohm's Law, and then converted into conductivity according to the known K factor of the solution. In some embodiments, conductivity is provided in logarithmically scaled measurement units, known in the art as Beta units. Since the conductivity of the solution is calculated according to the electrode voltage at the beginning of the DC pulse, the measured conductivity of the solution is not influenced by polarization. In this manner, present embodiments effectively compensate for polarization, and thereby produce a more accurate conductivity measurement, as compared to the prior art. As a result, present embodiments greatly reduce the likelihood of incorrect detergent concentrations resulting from erroneous conductivity measurements.

Like components in the Figures are similarly labeled.

DETAILED DESCRIPTION

Principles of the present invention are described below with reference to the industrial dishwasher 20 disclosed in U.S. Pat. No. 4,756,321, incorporated herein by reference, for simplicity only. It is to be understood that embodiments of the present invention may be used in other industrial dishwashers, or for any application in which it is desired to measure the conductivity of an aqueous solution. Accordingly, the present invention is not to be construed as limited to specific examples herein.

Figure 1:
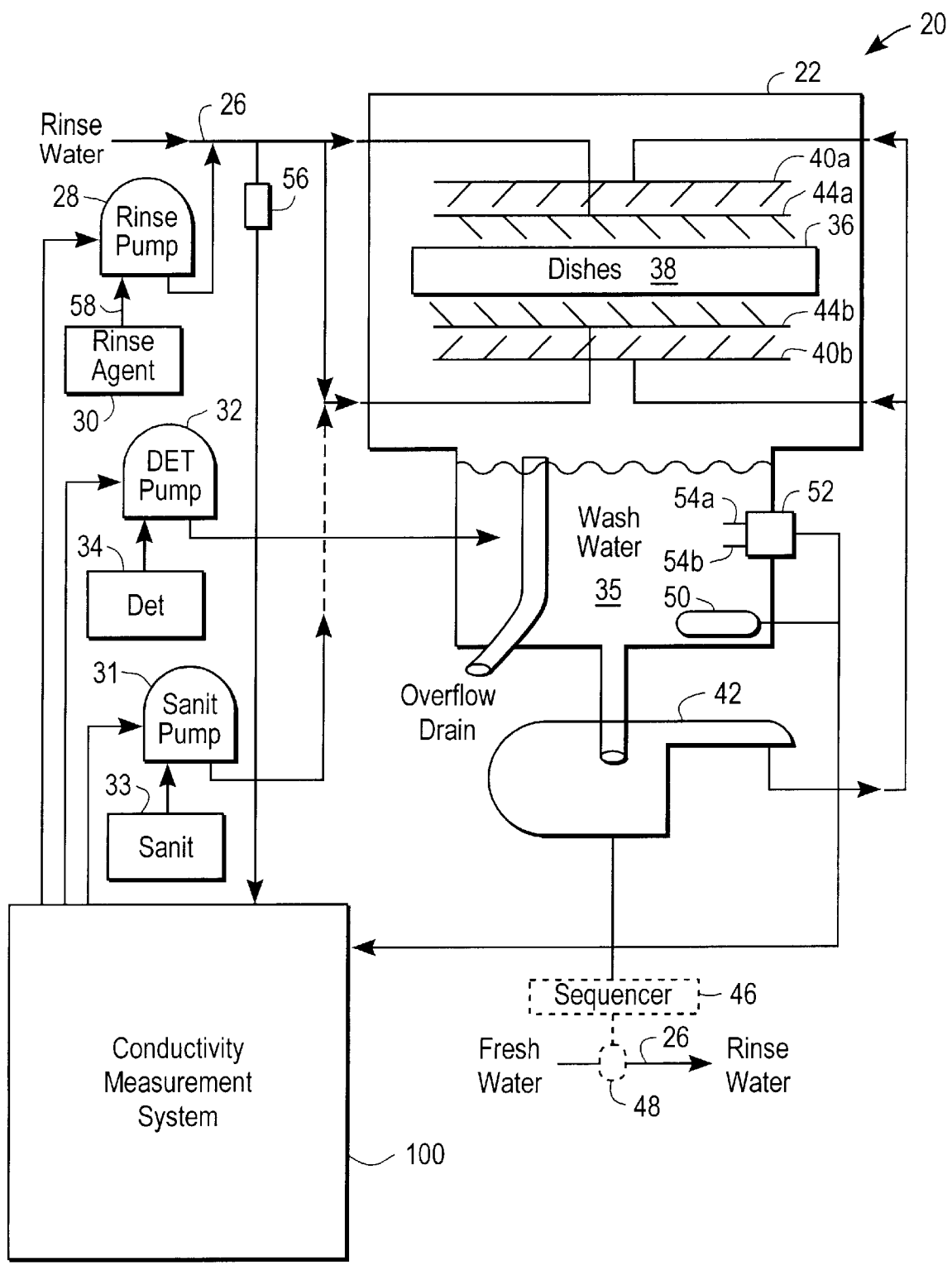
FIG. 1 is a block diagram of an industrial dishwasher in which a conductivity measurement system in accordance with the present invention is used.

Referring to FIG. 1, an industrial dishwasher 20 of the type described in U.S. Pat. No. 4,756,321 is shown to include a conductivity measurement system 100 in accordance with the present invention. System 100 is connected to a probe 52 having first 54a and second 54b electrodes submerged in a tank 35 of wash water used to wash dishes 38. In response to signals received from the probe 52, the system 100 provides control signals to a rinse pump 28, a detergent pump 32, and a sanitation pump 31 so as to ensure proper concentrations of a rinse agent, detergent, and a sanitation agent, respectively, within the wash water. For a discussion of the general operation of the dishwasher 20, as well as the advantages realized thereby, see U.S. Pat. No. 4,756,321.

Figure 2:
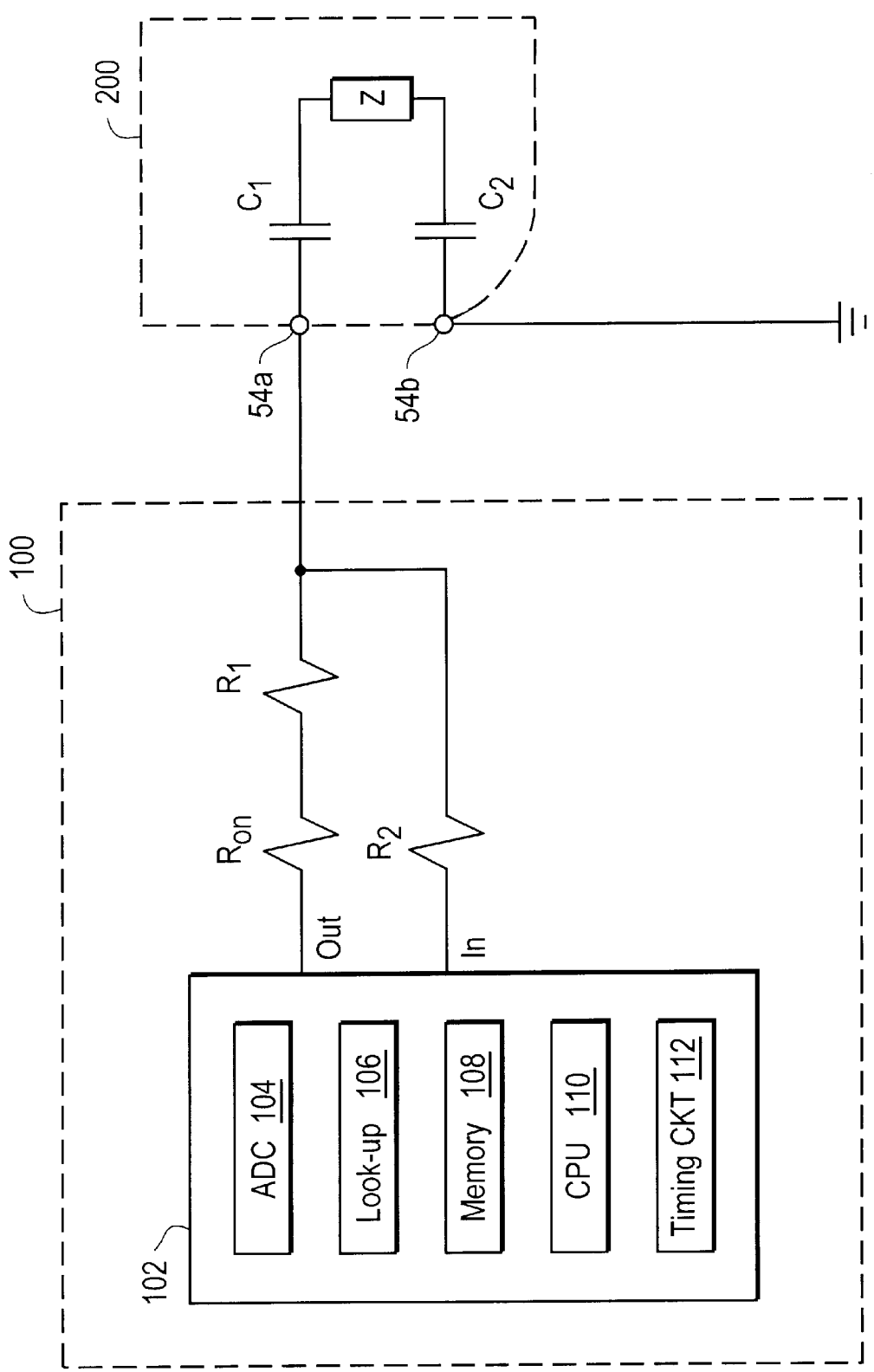
FIG. 2 is a block diagram of a micro-controller suitable for use in the conductivity measurement system of FIG. 1, including a schematic diagram of a four-layer capacitor modeling the polarization of wash water.

Referring to FIG. 2, the measurement circuit 100 includes a micro-controller 102 having an output terminal OUT coupled to the first electrode 54a via a resistor $R_1$, where resistor $R_{ON}$ models the on-resistance of the micro-controller 102. The resistor $R_1$ should be of a value suitable for the conductivity range of the wash water. In one embodiment, where $R_{ON}$ is 60Ω, a value of 200Ω is chosen for resistor $R_1$, as explained in detail below. The micro-controller 102 also has an input terminal IN coupled to the first electrode 54a via a resistor $R_2$ which serves as a series protection resistor for the ADC input terminal. Although the resistor $R_2$ should thus be as large as possible in order to provide maximum protection for the ADC input terminal, the resistor $R_2$ must also be small with respect to the input impedance of the ADC 104 in order to preserve signal strength. In one embodiment, where the micro-controller 102 is able to operate accurately with a source impedance as high as 10 kΩ, a value of 4.7 kΩ is selected for the resistor $R_2$. The second electrode 54b is tied to ground potential. Block 200 is an electrical representation on the wash water in the tank 35, where capacitors C1 and C2 form a four-layer capacitor which models polarization of the wash water, and the impedance element Z models the impedance of the wash water. Increases in electrode contamination are modeled by reducing the size of the capacitors.

The micro-controller 102 includes an analog-to-digital converter (ADC) 104, a look-up table 106, a memory 108, a central processing unit 110, and a timing circuit 112. The micro-controller 102 is connected to a voltage supply $V_{DC}$ and ground potential.

Figure 3:
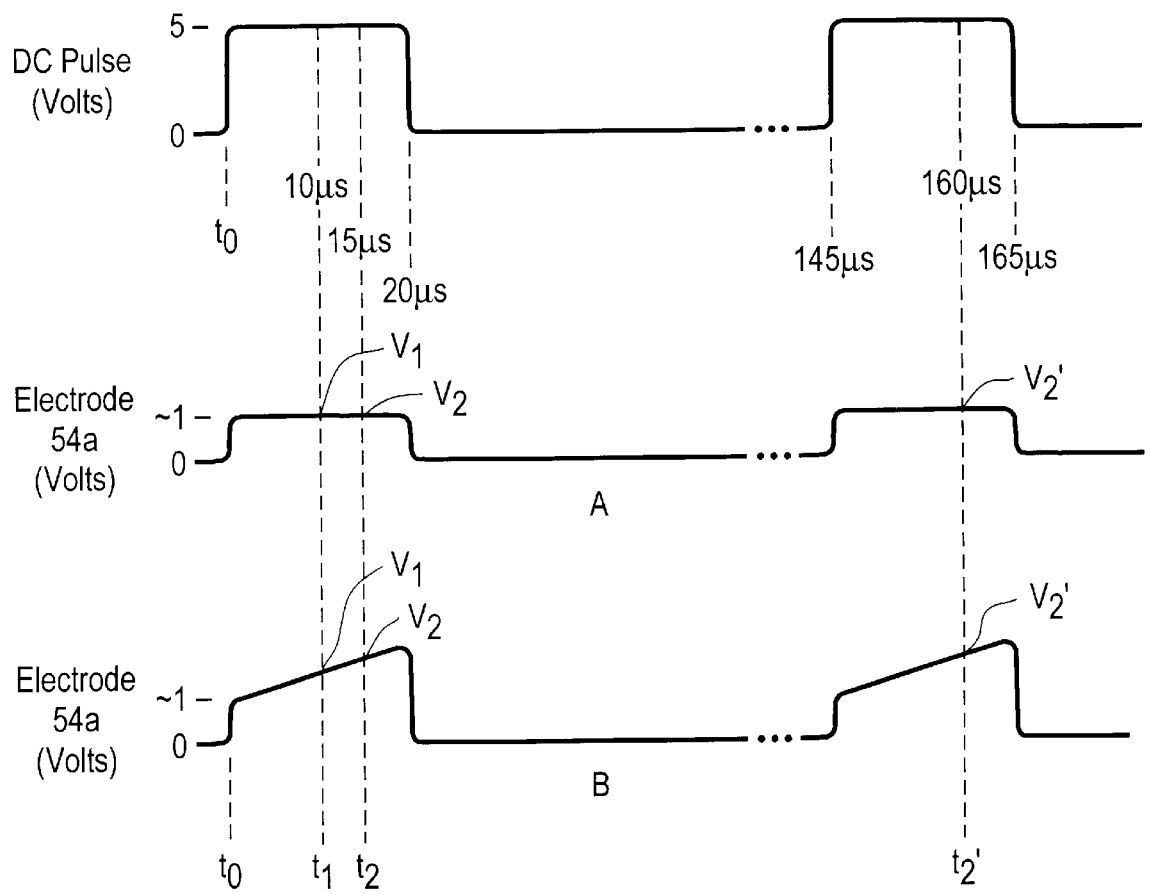
FIG. 3 is a timing diagram showing various signals associated with the operation of one embodiment of the present invention.

Referring also to the timing diagram of FIG. 3, the micro-controller 102 generates at its output terminal OUT a DC pulse having a duration of T and an amplitude equal to $V_{DC}$. The voltage at the electrode 54a is measured at times $t_1$ and $t_2$, where $t_1 < t_2 < T$, thereby giving measured voltages $V_1$ and $V_2$, respectively, which are stored in the memory 108. If there is no polarization within the wash water, the measured voltages $V_1$ and $V_2$ will be equal, as illustrated by case A of FIG. 3. If, on the other hand, there is polarization, the current flow between the electrodes 54a and 54b will decrease between times $t_1$ and $t_2$ and, therefore, the voltage $V_2$ will be greater than the voltage $V_1$, as illustrated by case B in FIG. 3. The rate at which the voltage at the electrode 54a changes is substantially linear and, therefore, compensation techniques discussed below utilize linear algorithms. However, where greater accuracy is desired, more complex, non-linear compensation techniques are used.

In calculating the conductivity of the wash water, linear regression is used to determine the voltage at electrode 54a at time t=0, i.e., at the beginning of the DC pulse. The voltage on the electrode 54a at time t=0 is given as:

$$V_0 = \frac{(V_1 * t_2) - (V_2 * t_2)}{(t_2 - t_1)}$$

Since the voltage $V_0$ corresponds to time t=0, the voltage $V_0$ is not influenced by the effects of polarization. Thus, the conductivity of the wash water, which is calculated using Ohm's law and the known K factor of the electrodes 54a and 54b, is not influenced by polarization within the wash water. In this manner, present embodiments compensate for polarization.

The difference between the first and second measured voltages, $V_{diff} = V_2 - V_1$, is indicative of the extent to which the electrodes are contaminated. Accordingly, if the difference value exceeds a predetermined threshold corresponding to the maximum degree of acceptable electrode contamination, the micro-controller 102 generates an alarm signal alerting an operator of the system 20 that the electrodes 54a and 54b need to be cleaned or replaced. Further, in some embodiments, if the measured voltage $V_0$ at time t=0 is greater than a second predetermined threshold, the micro-controller 102 generates an alarm signal alerting the operator that the electrodes 54a and 54b are sufficiently contaminated so as to require servicing. In this manner, present embodiments facilitate servicing of the electrodes 54a and 54b before contamination becomes sufficient to degrade conductivity measurement accuracy.

In preferred embodiments, an inexpensive micro-controller such as, for instance, the 16C72, 16C73, or the 16C74, all available from Microchip Semiconductor Corp. is used for the micro-controller 102 in order to minimize cost. Since these micro-controllers are typically unable to take quick successive analog measurements, the first and second voltage measurements, $V_1$ and $V_2$, are sampled during two separate pulses, as explained below, where $V_{DC}$=5 volts, $R_{ON}$=60Ω, $R_1$=200Ω, $R_2$=4.7 kΩ, $t_1$=10 μs, $t_2$=15 μs, T=20 μs, and K=0.4.

Figure 4:
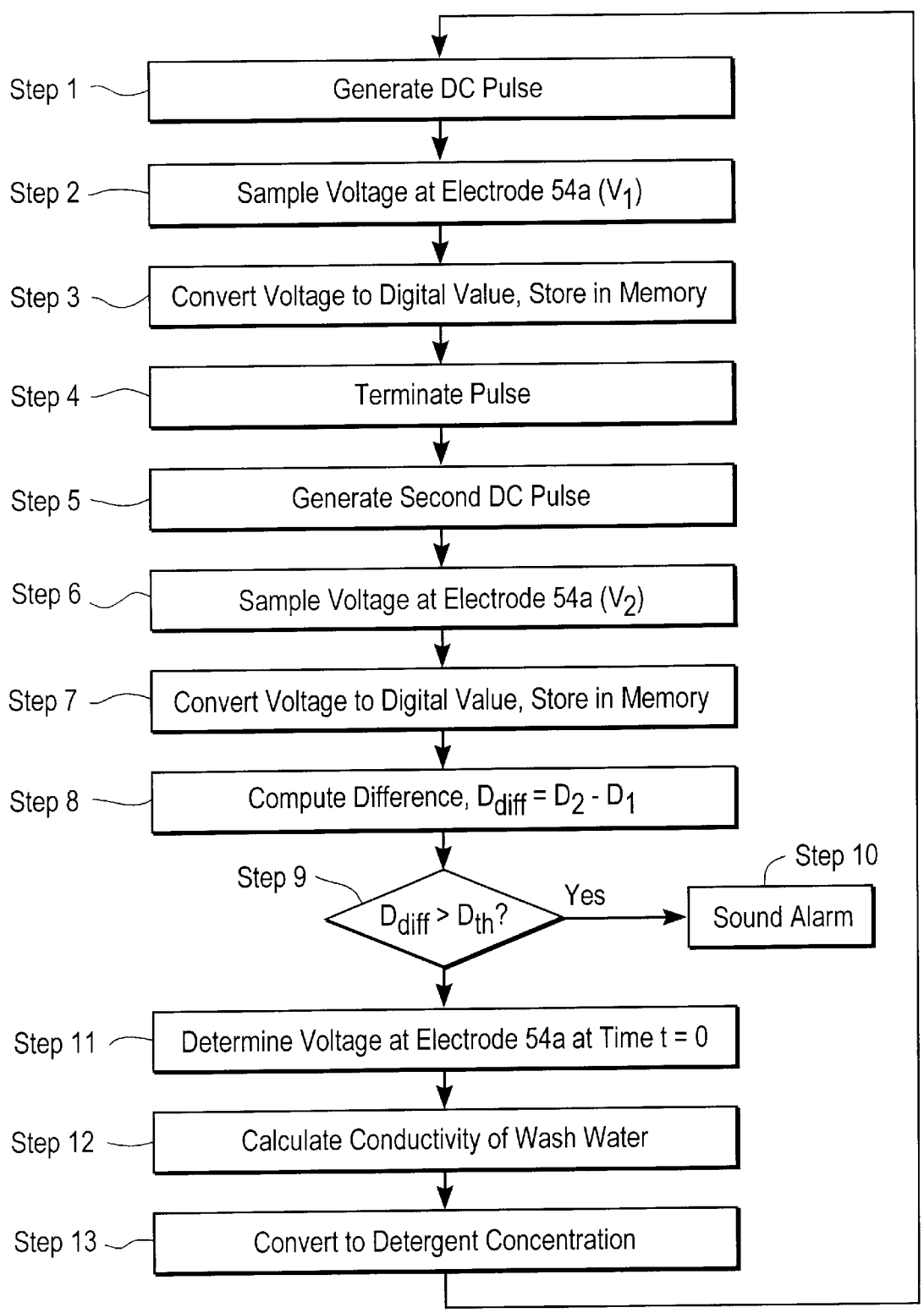
FIG. 4 is a flow chart illustrating operation of a conductivity measurement system in a preferred embodiment of the present invention.

Referring also to the flow chart of FIG. 4, the micro-controller 102 generates at time t=0 a first DC pulse having an amplitude of 5 volts (step 1). The DC pulse induces an electric field between the first and second electrodes 54a and 54b which, in turn, results in current flow between the electrodes 54a and 54b in the wash water. At time t=10 μs, the micro-controller 102 samples the voltage at the first electrode 54a via resistor $R_2$ (step 2). The resultant analog voltage $V_1$ is provided to the micro-controller 102 via its input terminal IN and is thereafter converted to a digital voltage $D_1$ via the ADC 104. The digital voltage $D_1$ is stored in the memory 108 (step 3). At time t=20 μs, the micro-controller 102 terminates the first pulse, and the electrode 54a discharges to ground potential (step 4). After a predetermined period of time such as, for instance, 125 μs, the micro-controller 102 generates at its output terminal OUT a second DC pulse having an amplitude of 5 volts (step 5). The micro-controller 102 samples the voltage at the first electrode 54a at a time 15 μs after the second pulse is initiated (step 6). The resultant analog voltage $V_2'$ is converted to a digital voltage $D_2'$ via the ADC 104, and stored in the memory 108 (step 7).

As mentioned above, the conductivity measuring system 100 alerts an operator of the dishwasher 20 when electrode contamination exceeds acceptable levels. Here, the CPU 110 of the micro-controller 102 calculates the difference between the first and second stored digital (binary) voltages, $D_{diff}$=$D_1$−$D_2'$ (step 8), and then compares the difference voltage $D_{diff}$ to a predetermined threshold voltage $D_{th}$ (step 9). If the difference voltage $D_{diff}$ exceeds the predetermined threshold voltage $D_{th}$, the micro-controller 102 activates an alarm signal to alert an operator of the dishwasher 20 that the electrodes need to be serviced (step 10).

The first and second voltages, $D_1$ and $D_2'$, are then processed by the CPU 110 according to the above-mentioned linear regression algorithm to determine the digital voltage $D_0$ on the first electrode 54a at the beginning of the first DC pulse, i.e., at time t=0 (step 11). In one embodiment, the digital voltages $D_1$ and $D_2'$ are stored as eight-bit numbers, where the binary number 255 corresponds to the analog value 5 (volts). This voltage at time t=0 and Ohm's Law are then used to calculate the conductance of the wash water (step 12). The conductance is converted to a detergent concentration using the look-up table 106 (step 13).

For example, where the digital voltages $D_1$ and $D_2'$ are equal to 65 and 70, respectively, the value $D_0$ (at time t=0) is equal to ((65)(15)−(70)(10))/(10+15)=55. The analog voltage $A_0$, which corresponds to the digital voltage $D_0$, is therefore equal to (5)(55)/(255)=1.08 volts. The current flowing in the circuit, i.e., through resistor $R_1$, is determined using Ohm's (V=IR). Here, the current is equal to (5−1.08)/(60+200)=0.0151 amps. The uncorrected resistance of the element Z, and thus the resistance of the wash water, is equal to (1.08)/(0.0148)=71.5Ω. The corrected resistance of the wash water is determined by dividing the uncorrected resistance by K, i.e., (71.5)/(.4)=178.75Ω, which gives a conductance of 1/(178.75)=0.00559 mhos (or siemens)=5590 μsiemans. This measured conductance corresponds to the beginning of the DC pulse, i.e., time t=0, and is thus not influenced by polarization. In this manner, the conductivity measurement system 100 avoids the polarization-induced, erroneous detergent concentration measurements characteristic of conventional conductivity measurement systems.

The K factor is indicative of the electrodes' sensitivity and is typically between 0.1 and 10, where electrodes having a small K factor are more suitable for measuring low conductances and, conversely, electrodes having a large K factor are more suitable for measuring large conductances. A cell formed of an electrode pair "sees" a conductance divided by the K factor, e.g., a cell having a K factor equal to 0.1 sees a conductance that is ten times larger than the actual conductance of the wash water.

In some embodiments, the micro-controller 102 converts the analog voltage $A_0$ into Beta units, a unit of measure especially suited for use in determining the conductance of a detergent solution in an industrial dishwasher. Beta units are well known in the art and are thus not discussed herein. For a detailed discussion of Beta units, see U.S. Pat. No. 4,756,321.

In the above example, the cell formed by electrodes 54a and 54b has a K factor equal to 0.4, the Beta Unit range is 60, and there are 3 counts per Beta Unit. The typical conductivity of wash water without detergent is about 600 μmhos, and the typical conductivity of wash water with a maximum detergent concentration is about 12,000 μmhos. Thus, the above cell formed by electrodes 54a and 54b actually "sees" wash water conductivities ranging from 600/0.4=1500 μmhos=0.0015 mhos to 12,000/0.4=30,000 μmhos=0.03 mhos. This conductivity range corresponds to a resistivity range of 1/(0.03 mhos)=33.3Ω to 1/(0.0015 mhos)=666.7Ω. Thus, the maximum Beta count, i.e., 180, corresponds to the minimum wash water conductance, i.e., $R_{WATER}$=666.7Ω. Using the voltage divider rule, $$\frac{180}{255} = \frac{666.7\Omega}{(R_{WATER} + R_{ON} + R1)}$$

where $R_{ON}$+$R_1$=277.8Ω. Since as mentioned earlier $R_{ON}$=60Ω, a value of about 200Ω is chosen for the resistor $R_1$. Applicants found that a value of 200Ω for resistor $R_1$ limited the current to a safe level.

In a preferred embodiment, the above-described pulse sequence is repeated every 250 ms so as to provide four conductivity measurements per second, although the interval between pulse sequences may be adjusted as desired for particular applications.

In the preferred embodiments, the conductivity measurement system 100 is implemented as software running on a micro-controller. Appropriate program modules may be stored on a CDROM, magnetic disk storage product, or any other computer readable data or program storage product. The software modules in the computer program product may also be distributed electronically, via the Internet or otherwise, by transmission of a computer data signal (in which the software modules are embedded) on a carrier wave.

While particular embodiments of the present invention have been shown and described, it will be obvious to those skilled in the art that changes and modifications may be made without departing from this invention in its broader aspects and, therefore, the appended claims are to encompass within their scope all such changes and modifications as fall within the true spirit and scope of this invention.

We claim:

1. A method of measuring representations of the electrical conductivity of an aqueous solution which compensates for polarization, said method comprising the steps of:

(a) providing first and second electrodes within said solution;

(b) generating, using a measurement circuit, a DC pulse to induce a current between said first and second electrodes;

(c) sampling the voltage at said first electrode at a first predetermined time interval after the generation of said DC pulse and generating a first voltage value in response thereto;

(d) sampling the voltage at said first electrode at a second predetermined time interval after the generation of said DC pulse and generating a second voltage value in response thereto;

(e) calculating, using linear regression and said first and second voltage values, the voltage at said first electrode contemporaneous with the generation of said DC pulse and generating a third voltage value in response thereto;

(f) producing, in response to said third voltage, a first signal representing the conductivity of said solution.

2. The method of claim 1, wherein said first predetermined time interval is approximately 10 $\mu$s.

3. The method of claim 2, wherein said second predetermined time interval is approximately 15 $\mu$s.

4. The method of claim 3, wherein said DC pulse has a duration of approximately 20 $\mu$s.

5. The method of claim 1, wherein said step (f) further comprises:

(f1) determining the current in said measurement circuit and generating a second signal in response thereto, said second signal representing the current in said solution;

(f2) dividing said second signal by said third voltage to generate said first signal representing the conductivity of said solution.

6. The method of claim 5, wherein said solution contains a detergent having a concentration, said method further comprising the steps of mapping, using a look-up table, said first signal representing the conductivity of said solution to a third signal representing the concentration of said detergent.

7. The method of claim 1, further comprising the steps of:

(g) subtracting said first voltage value from said second voltage value to generate a difference voltage;

(h) comparing said difference voltage to a predetermined threshold voltage; and (i) sounding an alarm if said difference voltage exceeds said predetermined threshold voltage, said alarm indicating that said electrodes are contaminated.

8. The method of claim 1, where:

in step (b) said DC pulse comprises first and second DC pulses;

in step (c), said first electrode is sampled at said first predetermined time interval after the generation of said first DC pulse to generate said first voltage value; and in step (d), said first electrode is sampled at said second predetermined time interval after the generation of said second DC pulse to generate said second voltage.

9. The method of claim 1, further comprising the step of:

(c1) generating, using said measurement circuit, a second DC pulse to induce current between said first and second electrodes;

wherein step (d) said first electrode is sampled at a second predetermined time after the generation of said second DC pulse.

10. A method of measuring representations of the electrical conductivity of an aqueous solution which compensates for polarization, the method comprising:

generating a DC pulse to induce a current between first and second electrodes positioned within the solution;

sampling a voltage at the first electrode at a first predetermined time interval after the generation of the DC pulse and generating a first voltage value in response thereto;

sampling the voltage at the first electrode at a second predetermined time interval after the generation of the DC pulse and generating a second voltage value in response thereto;

calculating, as a function of the first and second voltage values, a third voltage corresponding to the voltage at the first electrode at a time contemporaneous with the generation of the DC pulse; and generating a conductivity signal as a function of the third voltage, the conductivity signal representing the conductivity of the solution.

11. The method of claim 10, wherein generating the conductivity signal includes:

determining a current flowing between the first and second electrodes and generating a current value in response thereto, the current value representing the current flowing in the solution;

generating the conductivity signal as a function of the third voltage and the current value.

12. The method of claim 11, wherein the solution contains a detergent having a concentration, the method further comprising:

mapping, using a look-up table, the conductivity signal to a concentration signal representing the concentration of the detergent in the solution.

13. The method of claim 11, further comprising:

subtracting the first voltage value from the second voltage value to generate a difference voltage;

comparing the difference voltage to a predetermined threshold voltage; and generating an alarm signal if the difference voltage exceeds the predetermined threshold voltage, the alarm signal indicating that the electrodes are contaminated.

14. A method of measuring representations of the electrical conductivity of an aqueous solution which compensates for polarization, the method comprising:

generating first and second DC pulses to induce a current between first and second electrodes positioned within the solution;

sampling a voltage at the first electrode at a first predetermined time interval after the generation of one of the first and second DC pulses and generating a first voltage value in response thereto;

sampling the voltage at the first electrode at a second predetermined time interval after the generation of another one of the first and second DC pulses and generating a second voltage value in response thereto, wherein the one and the another one of the DC pulses are not the same DC pulse;

calculating, as a function of the first and second voltage values, a third voltage corresponding to the voltage at the first electrode at a time contemporaneous with the generation of either one of the DC pulses; and generating a conductivity signal as a function of the third voltage, the conductivity signal representing the conductivity of the solution.

15. The method of claim 14, wherein generating the conductivity signal includes:

determining a current flowing between the first and second electrodes and generating a current value in response thereto, the current value representing the current flowing in the solution;

generating the conductivity signal as a function of the third voltage and the current value.

16. The method of claim 15, wherein the solution contains a detergent having a concentration, the method further comprising:

mapping, using a look-up table, the conductivity signal to a concentration signal representing the concentration of the detergent in the solution.

17. The method of claim 15, further comprising:

subtracting the first voltage value from the second voltage value to generate a difference voltage;

comparing the difference voltage to a predetermined threshold voltage; and generating an alarm signal if the difference voltage exceeds the predetermined threshold voltage, the alarm signal indicating that the electrodes are contaminated.

18. Apparatus for measuring electrical conductivity of an aqueous solution, comprising:

a probe having first and second electrodes, for submersion in a tank containing the solution;

a circuit for generating a DC pulse to induce a current between the first and second electrodes within the solution; and a controller programmed to: sample voltage at the first electrode at first and second predetermined time intervals after the generation of the DC pulse; generate first and second voltage values in response to the sampling of the voltage at the first electrode at the first and second predetermined time intervals, respectively; calculate, as a function of the first and second voltage values, a third voltage corresponding to the voltage at the first electrode at a time contemporaneous with the generation of the DC pulse; and generate a conductivity signal as a function of the third voltage, the conductivity signal representing the conductivity of the solution.

19. The apparatus of claim 18, wherein the controller includes software executed by the controller for determining a current flowing between the first and second electrodes and generating a current value in response thereto, the current value representing the current in the solution, and for generating the conductivity signal as a function of the third voltage and the current value.

20. The apparatus of claim 19, wherein the solution contains a detergent having a concentration, and the controller includes software executed by the controller for mapping, using a look-up table, the conductivity signal to a concentration signal representing the concentration of the detergent in the solution.

21. The apparatus of claim 19, wherein the controller includes software executed by the controller for:

subtracting the first voltage value from the second voltage value to generate a difference voltage;

comparing the difference voltage to a predetermined threshold voltage; and generating an alarm signal if the difference voltage exceeds the predetermined threshold voltage, the alarm signal indicating that the electrodes are contaminated.

22. Apparatus for measuring electrical conductivity of an aqueous solution, comprising:

a probe having first and second electrodes, for submersion in a tank containing the solution;

a circuit for generating first and second DC pulses to induce a current between the first and second electrodes within the solution;

a controller programmed to: sample voltage at the first electrode at a first predetermined time interval after the generation of one of the first and second DC pulses and generating a first voltage value in response thereto; sample the voltage at the first electrode at a second predetermined time interval after the generation of another one of the first and second DC pulses and generating a second voltage value in response thereto, wherein the one and the another one of the DC pulses are not the same DC pulse; generate first and second voltage values corresponding to the sampled voltages; calculate as a function of the first and second voltage values, a third voltage corresponding to the voltage at the first electrode at a time contemporaneous with the generation of either one of the DC pulses; and generate a conductivity signal as a function of the third voltage, the conductivity signal representing the conductivity of the solution.

23. The apparatus of claim 22, wherein the controller includes software executed by the controller for determining a current flowing between the first and second electrodes and generating a current value in response thereto, the current value representing the current in the solution, and for generating the conductivity signal as a function of the third voltage and the current value.

24. The apparatus of claim 23, wherein the solution contains a detergent having a concentration, and the controller includes software executed by the controller for mapping, using a look-up table, the conductivity signal to a concentration signal representing the concentration of the detergent in the solution.

25. The apparatus of claim 23, wherein the controller includes software executed by the controller for:

subtracting the first voltage value from the second voltage value to generate a difference voltage;

comparing the difference voltage to a predetermined threshold voltage; and generating an alarm signal if the difference voltage exceeds the predetermined threshold voltage, the alarm signal indicating that the electrodes are contaminated.

26. Apparatus for measuring electrical conductivity of an aqueous solution, comprising:

a probe having first and second electrodes, for submersion in a tank containing the solution;

a circuit for generating one or more DC pulses to induce a current between the first and second electrodes within the solution;

means for sampling voltage at the first electrode at a first predetermined time interval after the generation of a respective DC pulse of the one or more DC pulses, and for sampling the voltage at the first electrode at a second predetermined time interval after the generation of a respective DC pulse of the one or more DC pulses; and means for generating first and second voltage values in response to the sampling of the voltage at the first electrode at the first and second predetermined time intervals, respectively, calculating, as a function of the first and second voltage values, a third voltage corresponding to the voltage at the first electrode at a time contemporaneous with the generation of any one of the one or more DC pulses; and generating a conductivity signal as a function of the third voltage, the conductivity signal representing the conductivity of the solution.

27. The apparatus of claim 26, wherein the generating means includes means for determining a current flowing between the first and second electrodes and generating a current value in response thereto, the current value representing the current in the solution, and for generating the conductivity signal as a function of the third voltage and the current value.

28. The apparatus of claim 27, wherein the solution contains a detergent having a concentration, and the generating means includes means for mapping, using a look-up table, the conductivity signal to a concentration signal representing the concentration of the detergent in the solution.

29. The apparatus of claim 27, wherein the means for generating includes means for:

subtracting the first voltage value from the second voltage value to generate a difference voltage;

comparing the difference voltage to a predetermined threshold voltage; and generating an alarm signal if the difference voltage exceeds the predetermined threshold voltage, the alarm signal indicating that the electrodes are contaminated.

* * * * *